United States Patent [19]

Suzuki et al.

[11] Patent Number: 5,447,933
[45] Date of Patent: Sep. 5, 1995

[54] XANTHINE DERIVATIVES

[75] Inventors: Fumio Suzuki, Mishima; Junichi Shimada, Shizuoka; Hiromasa Kato, Shizuoka; Akio Ishii, Shizuoka; Shizuo Shiozaki, Fuji, all of Japan

[73] Assignee: Kyowa Hakko Kogyo Co., Ltd., Tokyo, Japan

[21] Appl. No.: 973,959

[22] Filed: Nov. 9, 1992

[30] Foreign Application Priority Data

Nov. 8, 1991 [JP] Japan .................... 3-293269

[51] Int. Cl.⁶ .............. C07D 473/06; A61K 31/52
[52] U.S. Cl. ............................ 514/263; 544/267; 544/270; 544/272; 514/265
[58] Field of Search ............ 544/267, 270, 272, 273; 514/263

[56] References Cited

U.S. PATENT DOCUMENTS

| | | | |
|---|---|---|---|
| 4,576,947 | 3/1986 | Hinze et al. | 544/267 |
| 4,599,338 | 7/1986 | Regnier et al. | 544/270 |
| 4,879,296 | 11/1989 | Daluge et al. | 544/272 |
| 5,068,236 | 11/1991 | Suzuki et al. | 415/263 |
| 5,175,291 | 12/1992 | Kufner-Muhl | 544/272 |

FOREIGN PATENT DOCUMENTS

| | | |
|---|---|---|
| 724173 | 12/1965 | Canada .................. 260/241 |
| 0203721 | 3/1986 | European Pat. Off. . |
| 0374808 | 6/1990 | European Pat. Off. . |

(List continued on next page.)

OTHER PUBLICATIONS

Patel et al. Amer. Soc. Pharmacol. and Experimental Therapeutics; Mol. Pharm 33:585–91; 1989.

J. Linden et al., "¹²⁵I-Labeled 8-Phenylxanthine Derivatives: Antagonist Radioligands for Adenosine A₁ Re- (List continued on next page.)

*Primary Examiner*—Mukund J. Shah
*Assistant Examiner*—P. K. Sripada
*Attorney, Agent, or Firm*—Fitzpatrick, Cella, Harper & Scinto

[57] ABSTRACT

A novel xanthine derivative of the formula (I):

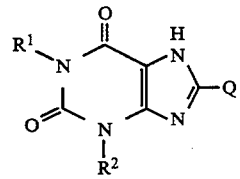

wherein one of $R^1$ and $R^2$ represents substituted or unsubstituted lower alkyl, lower alkenyl, lower alkynyl, substituted or unsubstituted alicyclic alkyl, substituted or unsubstituted phenyl, or substituted or unsubstituted benzyl; and the other represents $$-(CH_2)_m-X$$

wherein m is 2 or 3, and X is amino substituted phenyl. Q represents

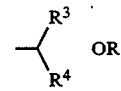

OR (wherein $R^3$ and $R^4$ are the same or different and are substituted or unsubstituted alicyclic alkyl),

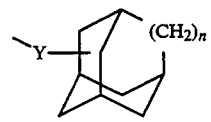

or a pharmacologically accetable salt thereof is disclosed. This derivative has anti-dementia activity.

5 Claims, No Drawings

FOREIGN PATENT DOCUMENTS

| | | |
|---|---|---|
| 0415456 | 3/1991 | European Pat. Off. |
| 0501379 | 9/1992 | European Pat. Off. |
| 0103497 | 3/1984 | France . |
| 62-42986 | 2/1987 | Japan . |
| 3173888 | 7/1991 | Japan . |
| 3173889 | 7/1991 | Japan . |
| WO8601724 | 3/1986 | WIPO . |
| WO00297 | 1/1992 | WIPO . |

OTHER PUBLICATIONS ceptors," *Journal of Medicinal Chemistry*, vol. 31, No. 4, Apr. 1988, pp. 745–751.

Shiozaki, et al., "Effects of KW–6055, A Novel Benzylpyridine Derivative, on Various Experimental Amnesia Models", Basic, Clinical and Therapeutic Aspects of Alzheimer's and Parkinson's Diseases, vol. 2 (1990), 449:52.

Merlos, et al., "Structure–Activity Relationships in a Series of Xanthine Derivatives", Eur. J. Med. Chem., vol. 25 (1990) 653:58.

Patel, et al., "$^{125}$I–BW–A844U, an Antagonist Radioligand with High Affinity and Selectivity for Adenosine $A_1$ Receptors", Mol. Pharmacol., vol. 33 (1988) 585:91.

XANTHINE DERIVATIVES

BACKGROUND OF THE INVENTION

The present invention relates to xanthine derivatives having anti-dementia activity and being useful as an anti-dementia drug.

Xanthine derivatives have been hitherto known in the prior art. For example, U.S. Pat. No. 5,068,236 (Japanese Published Unexamined Patent Application No. 173888/92) discloses xanthine derivatives of the formula:

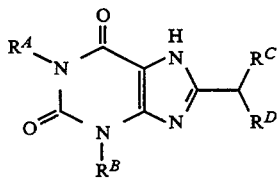

wherein $R^A$ and $R^B$ are lower alkyl; and $R^C$ and $R^D$ are substituted or unsubstituted alicyclic alkyl. The xanthine derivatives have exhibited diuretic activity, renal protecting activity and vasodilator activity.

EP 415456A (Japanese Published Unexamined Patent Application No. 173889/92) discloses xanthine derivatives of the formula:

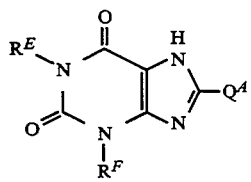

wherein $R^E$ and $R^F$ is lower alkyl; and $Q^A$ represents

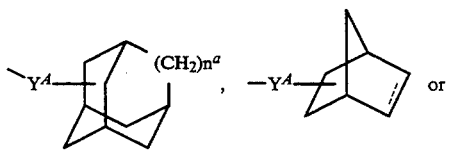

(wherein ═ is a single bond or double bond; $Y^A$ is a single bond or alkylene; and $n^a$ is 0 or 1).

Molecular Pharmacology, 33, 585 (1988) discloses a xanthine derivative of the formula:

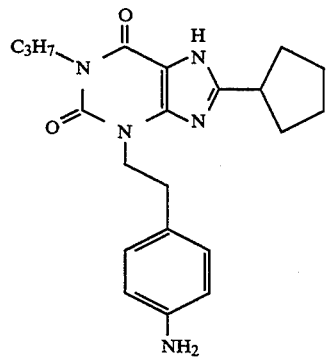

which has adenosine $A_1$ antagonistic activity.

Journal of Medicinal Chemistry, 31, 745 (1988) discloses a xanthine derivative of the formula:

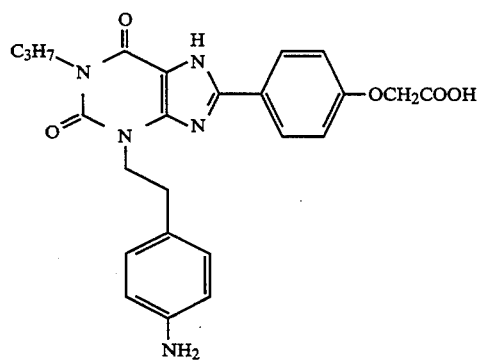

which has adenosine $A_1$ antagonistic activity.

European Journal of Medicinal Chemistry, 25, 653 (1990) discloses xanthine derivatives of the formula:

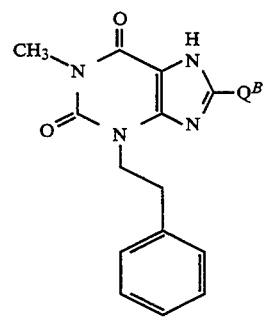

wherein $Q^B$ is alkyl. The xanthine derivatives have bronchodilator activity.

CP 724173 discloses xanthine derivatives of the formula:

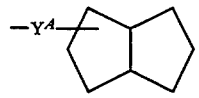

$R^G$ and $R^H$ are alkyl or aralkyl; and $Q^C$ is cycloalkyl. The xanthine derivatives have diuretic activity.

Further, WO 86/01724 discloses an insecticide containing xanthine derivatives of the formula:

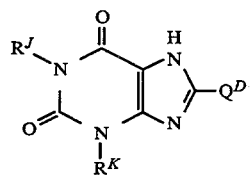

wherein $R^J$, $R^K$ and $Q^D$ and are substituted or unsubstituted aliphatic or alicyclic hydrocarbon having 1 to 8 carbon atoms (substituents are selected from halogen, alkyl and hydroxy) or substituted or unsubstituted aromatic hydrocarbon (substituents are selected from halogen, alkyl and hydroxy) or phenethyl.

EP 203721A (Japanese Published Unexamined Patent Application No. 42986/87) discloses xanthine derivatives of the formula:

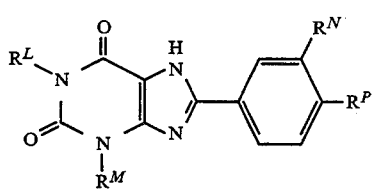

wherein $R^L$ and $R^M$ are alkyl or amino-substituted aralkyl; one of $R^N$ and $R^P$ is hydrogen and the other is —$Y^B$—Z (wherein $Y^B$ is alkenylene and Z is carboxy). The xanthine derivatives have adenosine antagonistic activity.

SUMMARY OF THE INVENTION

The object of the invention is to provide novel xanthine derivatives having excellent anti-dementia activity.

This object as well as other objects and advantages of the present invention will become apparent to those skilled in the art from the following description.

The present invention provides a xanthine derivative of the formula (I)

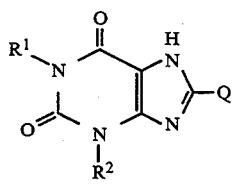

(I)

wherein either $R^1$ or $R^2$ represents substituted or unsubstituted lower alkyl, lower alkenyl, lower alkynyl, substituted or unsubstituted alicyclic alkyl, substituted or unsubstituted phenyl, or substituted or unsubstituted benzyl; and the other represents —(CH$_2$)$_m$—X, wherein m is 2 or 3, and X is

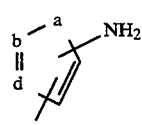

where a is NH, O or S, and b and d are the same or different and are CH or N, or

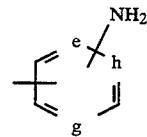

where e, g and h are the same or different and are CH or N; Q represents

(wherein $R^3$ and $R^4$ are the same or different and are substituted or unsubstituted alicyclicalkyl),

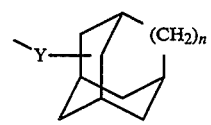

(wherein Y is single bond or alkylene; and n is 0 or 1),

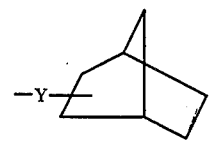

(wherein ═ is single or double bond, and Y is the same as defined above), or

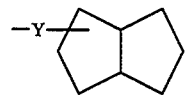

(wherein Y is the same as defined above); or a pharmacologically acceptable salt thereof.

DETAILED DESCRIPTION OF THE INVENTION

In the compound (I), examples of the alkyl moiety in the substituted or unsubstituted lower alkyl represented by $R^1$ and $R^2$ include straight or branched chain alkyl having 1 to 6 carbon atoms such as methyl, ethyl, propyl, isopropyl, butyl, isobutyl, sec-butyl, tert-butyl, pentyl, neopentyl, hexyl and the like. Substituents of the lower alkyl are alicyclic alkyl having 3 to 8 carbon atoms, for example, cyclopropyl, cyclobutyl, cyclopentyl, cyclohexyl, cyclooctyl and the like. Lower alkenyl includes straight or branched chain alkenyl having 2 to 4 carbon atoms such as vinyl, allyl, propenyl, isopropenyl, butenyl, isobutenyl and the like. Lower alkynyl includes straight or branched chain alkynyl having 2 to 4 carbon atoms such as propargyl, 3-butynyl and the like.

Examples of the alicyclic alkyl moiety in the substituted or unsubstituted alicyclic alkyl include cycloalkyl having 3 to 8 carbon atoms such as cyclopropyl, cyclobutyl, cyclopentyl, cyclohexyl, cyclooctyl and the like. The alicyclic alkyl, phenyl and benzyl may have 1 to 3 substituents and they are the same or different and are, for example, lower alkyl, hydroxy, lower alkoxy, halogen, nitro, amino and the like. The alkyl moieties of the lower alkyl and the lower alkoxy are the same as those described above. The halogen includes fluorine, chlorine, bromine and iodine.

Examples of the alkylene represented by Y include straight or branched chain alkylene having 1 to 4 carbon atoms such as methylene, ethylene, trimethylene, tetramethylene, methylmethylene, propylene, ethylethylene and the like.

The pharmacologically acceptable salt of the compound (I) includes pharmacologically acceptable acid addition salts, metal salts, ammonium salts, organic amine addition salts, amino acid addition salts and the like.

As the pharmacologically acceptable acid addition salt, there are salts formed with inorganic acids such as hydrochloride, sulfate, phosphate and the like, salts formed with organic acids such as acetate, maleate, fumarate, tartrate, citrate and the like. As the metal salt, there are alkali metal salts such as sodium salt, potassium salt and the like, alkaline earth metal salts such as magnesium salt, calcium salt and the like, aluminum salt and zinc salt. As the ammonium salts, there are ammonium salt, tetramethylammonium salt and the like. As the organic amine addition salt, there are morpholine addition salt, piperidine addition salt and the like. As the amino acid addition salt, there are lysine addition salt, phenylalanine addition salt and the like.

The compound (I) can be produced according to the following reaction scheme:

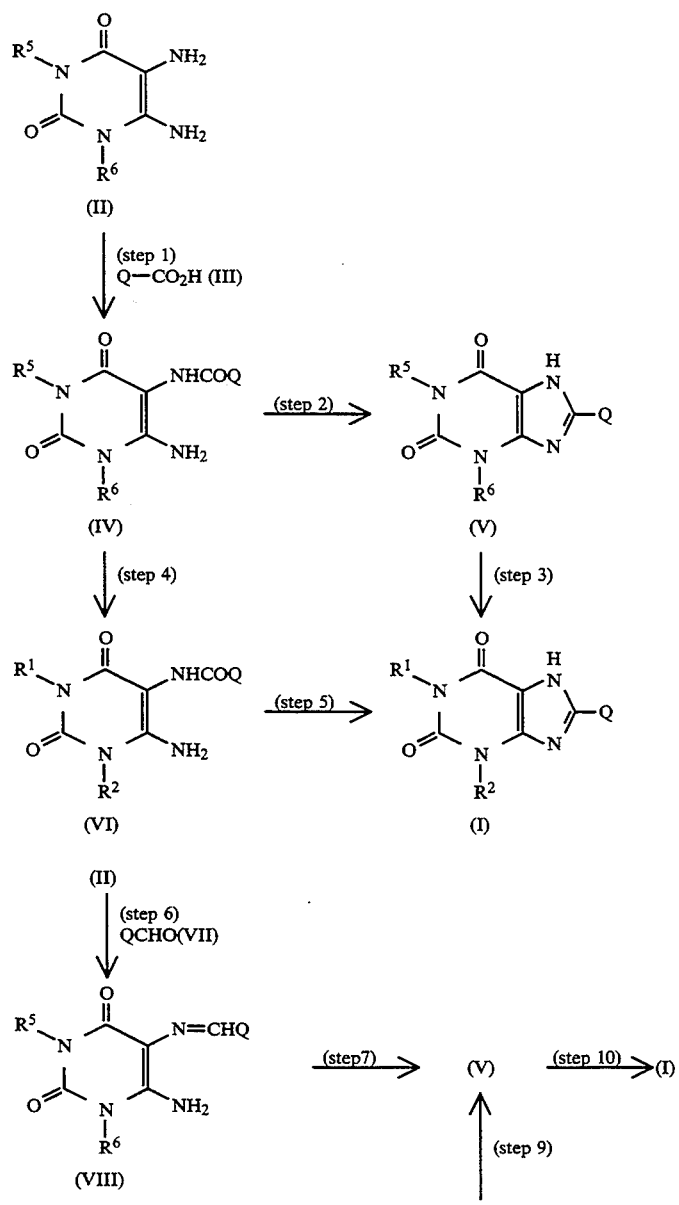

[Structural formulas showing compound (IX) with R⁵, Hal substituents converting via step 8 (H₂NCH₂Q(X)) to compound (XI) with R⁶, NHCH₂Q substituents]

wherein one of $R^5$ and $R^6$ is substituted or unsubstituted lower alkyl, lower alkenyl, lower alkynyl, substituted or unsubstituted alicyclic alkyl, substituted or unsubstituted phenyl, or substituted or unsubstituted benzyl, and the other is —$(CH_2)_m$—$X^4$, wherein m is the same as defined above, and $X^4$ is

[Structural formula showing vinyl group with a, b, d positions and NHP substituent]

or

[Structural formula showing aromatic ring with e, g, h positions and NHP substituent]

wherein a, b, d, e, g and h are the same as defined above, and P is a protecting group of the amino group; Hal is halogen; and $R^1$, $R^2$ and Q are as defined above.

As the protecting group, there are tertbutoxycarbonyl, benzyloxycarbonyl, acetyl, formyl and the like. Halogen is the same as defined above.

Each step is explained below.

Step 1

The compound (IV) is obtained by reacting the compound (II) which can be obtained according to a known method (for example, EP 103497A) with the compound (III) or a reactive derivative thereof.

As the reactive derivative of the compound (III), for example, there are acid halides such as acid chloride, acid bromide and the like, active esters such as p-nitrophenyl ester, N-oxysuccinimide and the like, acid anhydrides obtained by using carbodiimide such as 1-ethyl-3-( 3-dimethylaminopropyl)carbodiimide, diisopropylcarbodiimide, dicyclohexylcarbodiimide and the like, mixed acid anhydrides with monoethyl carbonate ester, monoisobutyl carbonate ester and the like.

In this reaction, the compound (III) is used in an amount of 1 to 5 equivalents per 1 equivalent of the compound (II).

When the compound (III) is used, the reaction is carried out by heating to 50° to 200° C. in the absence of a solvent. When the reactive derivative is used, the reaction can be carried out according to a common method in the field of peptide chemistry. For example, the reaction can be carried out in a solvent selected from halogenated hydrocarbons such as methylene chloride, chloroform, ethane dichloride and the like, ethers such as dioxane, tetrahydrofuran and the like, dimethylformamide, dimethyl sulfoxide, if necessary, water and the like. The reaction is carried out at a temperature of −80 to 50° C. and is completed within 0.5 to 24 hours. If necessary, the reaction can be carried out in the presence of an additive such as 1-hydroxybenzo-triazole or the like, or a base such as pyridine, triethylamine, 4-dimethylaminopyridine, N-methylmorpholine or the like.

Step 2

The compound (V) is obtained by ring closure reaction of the compound (IV) in the presence of a base (Process A), by treatment with a dehydrating agent (Process S), or by heating (Process C).

Process A

The compound (V) is obtained by reacting the compound (IV) at a temperature of 4° C. to 180° C. for 10 minutes to 6 hours in a solvent in the presence of a base.

As the base, there are alkali metal hydroxides such as sodium hydroxide, potassium hydroxide and the like.

As the solvent, there are water, lower alkanols such as methanol, ethanol and the like, ethers such as dioxane, tetrahydrofuran and the like, dimethylformamide, dimethyl sulfoxide and the like. These solvents can be used alone or in combination thereof.

Process B

The compound (V) is obtained by reacting the compound (IV) at a temperature of 4° C. to 180° C. for 0.5 to 12 hours in a solvent or without any solvent in the presence of a dehydrating agent.

As the dehydrating agent, there are thionyl halides such as thionyl chloride and the like, phosphorus oxyhalides such as phosphorus oxychloride and the like. As the solvent, there are halogenated hydrocarbons such as methylene chloride, chloroform, ethane dichloride and the like, dimethylformamide, dimethyl sulfoxide and the like.

Process C

The compound (V) is obtained by heating the compound (IV) at 50° to 200° C. for 1 to 20 hours in a solvent.

As the solvent, there are dimethylformamide, dimethyl sulfoxide, Dowthermo A (manufactured by Dow Chemical Co., U.S.A.) and the like.

Step 3

The compound (I) is obtained by deprotecting the protecting group P of the compound (V) according to a conventional method employed in the field of synthetic organic chemistry.

When the protecting group P is, for example, benzyloxycarbonyl group, catalytic hydrogenation is carried out with hydrogen gas in a solvent at an atmospheric pressure in the presence of a hydrogenation catalyst. The reaction is carried out at a temperature of 4° C. to 100° C. for 0.5 to 48 hours.

As the hydrogenation catalyst, there are platinum catalysts such as platinum oxide, activated carbon on platinum (Pt/C) and the like, palladium catalysts such as activated carbon on palladium (Pd/C), palladium black and the like, nickel catalysts such as Raney nickel and the like, activated carbon on rhodium (Rh/C) and the like. As the solvent, there are alcohols such as methanol, ethanol and the like, esters such as ethyl acetate and the like, ethers such as dioxane, tetrahydrofuran and the like, N,N-dimethylformamide, acetic acid and the like.

Step 4

The compound (VI) is obtained from the compound (IV) according to the same manner as that described in Step 3.

Step 5

The compound (I) is obtained from the compound (VI) according to the same procedure as that described in Step 2.

Step 6

The compound (VIII) is obtained by reacting the compound (II) with the compound (VII) at −80° to 100° C. for 10 minutes to 5 hours in a solvent.

In the reaction, the compound (VII) is used in an amount of 1 to 2 equivalents per 1 equivalent of the compound (II).

As the solvent, there are mixed solvents of acetic acid with lower alcohols such as methanol, ethanol and the like.

Step 7

The compound (V) is obtained by reacting the compound (VIII) at 4° C. to 180° C. for 30 minutes to 10 hours in a solvent in the presence of an oxidizing agent.

As the oxidizing agent, there are oxygen, ferric chloride, ammonium cerium (IV) nitrate, diethylazodicarboxylate and the like. As the solvent, there are lower alcohols such as methanol, ethanol and the like, halogenated hydrocarbons such as methylene chloride, chloroform and the like, aromatic hydrocarbons such as toluene, xylene, nitrobenzene and the like.

Step 8

The compound (XI) is obtained by reacting the compound (X) and the compound (IX) at a temperature of 50° to 150° C. for 30 minutes to 10 hours.

In the reaction, the compound (X) is used in an amount of 1 to 2 equivalents per 1 equivalent of the compound (IX).

As the solvent, there are lower alcohols such as methanol, ethanol and the like, dimethylformamide, dimethyl sulfoxide and the like.

Step 9

The compound (V) is obtained by reacting the compound (XI) and a nitrosating agent at a temperature of 4° C. to the boiling point of the solvent for 30 minutes to 10 hours in a solvent in the presence of an acid.

In the reaction, the nitrosating agent is used in an amount of 1 to 3 equivalents per 1 equivalent of the compound (XI).

As the nitrosating agent, there are nitrous acid derivatives such as sodium nitrite, isoamyl nitrite and the like. As the acid, there are acetic acid, dilute hydrochloric acid and the like. As the solvent, there are lower alcohols such as methanol, ethanol and the like.

Step 10

The compound (I) is obtained from the compound (V) according to the same procedure as that described in Step 3.

The desired compounds in the above respective steps can be isolated and purified by a conventional purification method usually employed in the field of synthetic organic chemistry such as filtration, extraction, washing, drying, concentration, recrystallization, various chromatographic processes and the like.

The salt of the compound (I) can be obtained by a conventional method usually employed in the field of synthetic organic chemistry. For example, when the compound (I) is obtained in a salt form, it may be purified as it is. When the compound (I) is obtained in the free form, it may be dissolved or suspended in a suitable solvent and thereafter an acid or base may be added thereto to form a salt.

In addition, the compound (I) or pharmacologically acceptable salt thereof may be in an addition form of water or various solvents, and these addition forms are included in the scope of the present invention.

Further, the compound (I) can exist in the form of optical isomers. The present invention includes all possible stereoisomers or mixture thereof including the optical active isomer.

The examples of the compound (I) are shown in Table 1.

TABLE 1

| Compound No. | R¹ | R² | Q |
|---|---|---|---|
| 1 | n-$C_3H_7$ | —$CH_2CH_2$—C₆H₄—$NH_2$ | 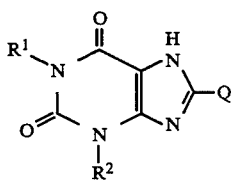 |
| 2 | —$CH_2CH_2$—C₆H₄—$NH_2$ | n-$C_3H_7$ | 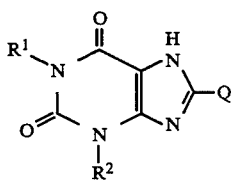 |

TABLE 1-continued

| Compound No. | R¹ | R² | Q |
|---|---|---|---|
| 3 | n-C₃H₇ | —CH₂CH₂—C₆H₄—NH₂ | dicyclopropylmethyl |
| 4 | —CH₂CH₂—C₆H₄—NH₂ | n-C₃H₇ | dicyclopropylmethyl |
| 5 | n-C₃H₇ | —CH₂CH₂—C₆H₄—NH₂ | cis-bicyclo[3.3.0]octyl |
| 6 | n-C₃H₇ | —CH₂CH₂—C₆H₄—NH₂ | norbornyl |

The pharmacological activity of the compound (I) is illustrated by the following experiment:

Experimental Data

The effect of Compound (I) on dementia was determined by scopolamine induced amnesia models (Basic. Clinical. and Therapeutic Aspects of Alzheimer's and Parkinson's Diseases; Vol. 2; T. Nagatsu, et al. edt; pp449; Plenum Press New York; 1990).

Male whister rats (Charles River Laboratories) weighing 220 g to 280 g were used for the test, and each group consisted of 12 to 13 animals. The test was performed with a step-through type passive avoidance apparatus (the bright and dark box).

The bright and dark box was made up of a bright compartment (25×25×25 cm) lighted by 4W white luminescent and a dark compartment (25×25×25 cm). These two compartments were partitioned by a guillotine door (9×9 cm) and had a grid floor of stainless steel. In order to give a foot shock, the electric current (2 mA: 2 sec) may be passed through the grid floor of the dark compartment.

The compound to be tested was suspended in 0.3% aqueous carboxymethyl cellulose solution and the suspension was orally administered 60 minutes before the acquired trial (only 0.3% aqueous carboxymethyl cellulose solution was given to the control group).

Amnesia treatment was carried out by intraperitoneally administering 1 mg/kg of scopolamine 30 minutes before the following acquired trial.

The training for acquisition of learning (acquired trial) was carried out. The rat was then introduced into the bright compartment and, after 5 to 10 seconds, the guillotine door was opened. The rat in the bright compartment rapidly moved into the dark compartment. As soon as the whole body of the rat entered into the dark compartment, the guillotine door was closed. An electric current of 2 mA was immediately passed through the grid floor for two seconds (foot shock). After the trial, the rat receiving the foot shock (acquisition of learning) was taken out of the dark compartment.

A test trial (retention trial) was carried out for observing the retention and recall of the memory, as follows. Twenty-four hours after the acquired trial, the rat was placed in the bright compartment and the guillotine door was opened. The time required from opening of the guillotine door to movement of the rat from the bright compartment into the dark compartment (latency) was measured. The time (latency) was measured up to 600 seconds and the time of over 600 seconds was regarded as 600 seconds.

In the experiment, the amnesia control group had undergone amnesia treatment and the normal control group had not undergone amnesia treatment.

Latency of test compound treated group and latency of amnesia control group were compared in Table 2. In Table 2, test of significance was performed by Mann Whitney U-test.

TABLE 2

| Test compound | Dose (mg/kg; p.o.) | Amnesia treatment | Number of animals | Recall trial mean reaction latent time (sec.) | Comparison to amnesia control |
|---|---|---|---|---|---|
| Normal control | 0 | — | 10 | 557.8 ± 32.8 | — |
| Amnesia control | 0 | + | 15 | 13.5 ± 3.0 | * |
| Compound 1 | 0.02 | + | 15 | 22.9 ± 5.5 | not significant |
|  | 0.08 | + | 15 | 20.5 ± 3.5 | not significant |
|  | 0.31 | + | 15 | 95.9 ± 41.1 | $p < 0.01$ |
|  | 1.25 | + | 15 | 136.4 ± 41.9 | $p < 0.001$ |
|  | 5.0 | + | 15 | 182.3 ± 57.5 | $p < 0.01$ |
|  | 20.0 | + | 15 | 231.4 ± 76.2 | $p < 0.001$ |
| Normal control | 0 | — | 13 | 557.4 ± 21.6 | — |
| Amnesia control | 0 | + | 19 | 33.8 ± 11.5 | * |
| Compound 3 | 0.02 | + | 14 | 47.7 ± 16.4 | not significant |
|  | 0.08 | + | 14 | 119.2 ± 45.2 | $p < 0.05$ |
|  | 0.31 | + | 14 | 152.6 ± 41.7 | $p < 0.001$ |
|  | 1.25 | + | 14 | 70.8 ± 41.7 | not significant |
|  | 5.0 | + | 14 | 66.9 ± 33.8 | not significant |
| Normal control | 0 | — | 13 | 557.4 ± 21.6 | — |
| Amnesia control | 0 | + | 20 | 44.2 ± 10.8 | * |
| Compound 4 | 0.02 | + | 15 | 117.7 ± 38.2 | $p < 0.05$ |
|  | 0.08 | + | 15 | 216.9 ± 57.9 | $p < 0.01$ |
|  | 0.31 | + | 15 | 106.5 ± 40.9 | not significant |
|  | 1.25 | + | 15 | 199.5 ± 64.0 | $p < 0.05$ |
|  | 5.0 | + | 15 | 105.3 ± 31.8 | $p < 0.05$ |

* Latency of amnesia control group is significantly lower than latency of normal control, ($p < 0.001$).

Acute Toxicity Test

The compound 1, 2, 3 and 4 were orally administered to dd strain male mice (body weight: 20±1 g, 3 mice/group). The lethal state was observed 7 days after administration to obtain the minimum lethal dose (MLD).

MLD of the all compounds were >300 mg/kg. This is weak toxicity and therefore the compound can be used safely in a wide dose range.

The compound (I) or a pharmacologically acceptable salt thereof can be used as it is or in various pharmaceutical composition forms.

The pharmaceutical composition of the present invention can be prepared by uniformly mixing an effective amount of the compound (I) or a pharmacologically acceptable salt thereof as an active component with a pharmacologically acceptable carrier. The pharmaceutical composition are preferably in the form of a unit dosage form suitable for oral administration or injection.

For preparing a pharmaceutical composition for oral administration, any useful pharmacologically acceptable carrier or diluent can be used. For example, suspensions and syrups can be prepared using water, sugars such as sucrose, sorbitol, fructose and the like, glycols such as polyethylene glycol, propylene glycol and the like, oils such as sesame oil, olive oil, soybean oil and the like, preservatives such as p-hydroxybenzoic acid esters and the like, flavors such as strawberry flavor, peppermint and the like. Powders, pills, capsules and tablets can be prepared using excipients such as lactose, glucose, sucrose, mannitol and the like, disintegrating agents such as starch, sodium alginate and the like, lubricants such as magnesium stearate, talc and the like, binders such as polyvinyl alcohol, hydroxypropyl cellulose, gelatin and the like, surfactants such as fatty acid esters and the like, plasticizers such as glycerin and the like. Tablets and capsules are most useful oral unit dosage forms because of easy administration.

Injectable preparations can be prepared using a carrier such as distilled water, a salt solution, glucose solution or mixture of a salt solution and glucose solution. The preparations can be prepared in the form of solutions, suspensions or dispersions by using a suitable method.

The compound (I) or a pharmacologically acceptable salt thereof can be administered orally in the said dosages forms or parenterally as injections. The effective dosage regimen and administration route vary depending upon a particular dosage form and particular age, weight and conditions of the patient. However, normally, the compound (I) or a pharmacologically acceptable salt thereof is administered in the amount of 0.02 to 50 mg/kg per day and the dosage can be divided to be administered 3 to 4 times per day.

The following Examples and Reference Examples further illustrate the present invention in detail but are not to be construed to limit the scope thereof.

EXAMPLE 1

3-Noradamantanecarboxylic acid (2.79 g, 16.8 mmol) was dissolved in a mixture of tetrahydrofuran (50 ml) and methylene chloride (50 ml). 1-Hydroxybenzotriazole (2.57 g, 16.8 mmol) and 1-ethyl-3-(3-dimethylamino)propylcarbodiimide hydrochloride (3.22 g, 16.8 mmol) were added at 0° C., and reacted at room temperature for 4 hours. To the resulting solution, 4-dimethylaminopyridine (170 mg, 1.4 mmol); followed by a solution of 5,6-diamino-1-(4-benzyloxycarbonylaminophenethyl)-3-propyluracil (6.12 g, 14.0 mmol: obtained in Reference Example 1) in a mixture of N,N-dimethylformamide (20 ml) and tetrahydrofuran (40 ml) were added. After reacting for one hour, the reaction mixture was concentrated by reducing the volume in halves. After the addition of water (100 ml)

to the concentrated mixture, the mixture was extracted three times with chloroform. The organic layers were combined, washed with an aqueous saturated solution of sodium chloride, dried over sodium sulfate, and the solvent was evaporated under reduced pressure. The residue was isolated and purified by silica gel column chromatography (eluent: 2% methanol/98% chloroform) to obtain 6-amino-5-(3-noradamantane)-carbonylamino- 1-(4-benzyloxycarbonylaminophenethyl)-3-propyluracil (6.95 g, yield: 85%).

NMR (90 MHz; CDCl$_3$) δ(ppm): 7.99 (1H, brs), 7.50–7.25 (7H, m), 7.12 (2H, d, J=7.8 Hz), 6.89 (1H, brs), 5.20 (2H, s), 4.25–3.65 (6H, m), 3.05–2.75 (3H, m), 2.45–1.45 (14H, m), 0.90 (3H, t, J=7.0 Hz)

The resulting compound (6.81 g, 11.6 mmol) was dissolved in ethanol (200 ml) and the catalyst 10% Pd/C (600 mg) was added thereto. The mixture was stirred for 15 hours under hydrogen. The catalyst was removed by filtration, washed with ethanol and the filtrate was concentrated. The residue was purified on silica gel column chromatography (eluent: 5% methanol/95% chloroform) and triturated with diethyl ether/hexane=3/1 (v/v) to obtain 6-amino-1-(4-aminophenethyl)-5-(3-noradamantane)carbonylamino-3-propyluracil (3.65 g, yield: 69%).

NMR (90 MHz; CDCl$_3$) δ(ppm): 7.32 (1H, brs), 6.97 (2H, d, J=8.5 Hz), 6.60 (2H, d, J=8.5 Hz), 5.28 (2H, brs), 4.20–3.75 (4H, m), 3.27 (2H, brs), 3.00–2.75 (3H, m), 2.45–1.45 (14H, m), 0.96 (3H, t, J=7.0 Hz)

The resulting compound (3.50 g, 7.75 mmol) was dissolved in dioxane (80 ml). 1N Aqueous solution (240 ml) of sodium hydroxide was added thereto. The mixture was heated under reflux for 1 hour. After cooling, the solution was neutralized with conc. hydrochloric acid, and the precipitated crystals were filtered, dried under reduced pressure and recrystallized from tetrahydrofuran to obtain 3-(4-aminophenethyl)-8-(3-noradamantyl)-1-propylxanthine (compound 1) (1.33 g, yield: 40%).

Melting point: 283.7°–285.2° C.
Elementary analysis for C$_{25}$H$_{31}$N$_5$O$_2$,
Calc. (%): C 69.25, H 7.20, N 16.15
Found (%): C 69.38, H 7.48, N 16.17
IR (KBr) ν$_{max}$ (cm$^{-1}$): 1694, 1644, 1554, 1519, 1494
NMR (270 MHz; DMSO-d$_6$) δ(ppm): 13.0 (1H, brs), 6.83 (2H, d, J=8.4 Hz), 6.46 (2H, d, J=8.4 Hz), 4.86 (2H, brs), 4.10 (2H, t, J=7.4 Hz), 3.83 (2H, t, J=7.4 Hz), 2.78 (2H, t, J=7.4 Hz), 2.61 (1H, t, J=6.5 Hz), 2.35–2.25 (2H, m), 2.20–2.10 (2H, m), 2.00–1.85 (4H, m), 1.70–1.50 (6H, m), 0.86 (3H, t, J=8.0 Hz)
MS (m/e): 433 (M+)

EXAMPLE 2

3-(4-Aminophenethyl)-8-(3-noradamantyl)-1-propylxanthine (compound 2, 0.32 g) was obtained (yield: 37%) according to the same manner as that described in Example 1, except that 3-noradamantanecarboxylic acid (0.40 g, 2.41 mmol) and 5,6-diamino-3-(4-benzyloxycarbonyl-aminophenethyl)-1-propyluracil (0.87 g, 2.01 mmol) obtained in Reference Example 2 were used instead of 3-noradamantanecarboxylic acid (2.79 g, 16.8 mmol) and 5,6-diamino-1-(4-benzyloxycarbonylaminophenethyl)-3-propyluracil (6.12 g, 14.0 mmol) obtained in Reference Example 1.

Melting point: 244.6°–245.1° C.
Elementary analysis for C$_{25}$H$_{31}$N$_5$O$_2$,
Calc. (%) C 69.25, H 7.20, N 16.15
Found (%) C 69.06, H 7.26, N 15.95
IR (KBr) ν$_{max}$ (cm$^{-1}$): 1694, 1657, 1645, 1547, 1518, 1493
NMR (270 MHz; DMSO-d$_6$) δ(ppm): 12.92 (1H, brs), 6.87 (2H, d, J=7.9 Hz), 6.48 (2H, d, J=7.9 Hz), 4.87 (2H, brs), 3.99 (2H, t, J=7.9 Hz), 3.95 (2H, t, J=7.4 Hz), 2.65–2.55 (3H, m), 2.30–2.25 (2H, m), 2.20–2.10 (2H, m), 2.00–1.85 (4H, m), 1.75–1.55 (6H, m), 0.87 (3H, t, J=7.4 Hz)
MS (m/e): 433 (M+)

EXAMPLE 3

3-(4-Aminophenethyl)-8-dicyclopropylmethyl-1-propylxanthine (compound 3, 0.28 g) was obtained (yield: 13%) according to the same manner as that described in Example 1 except that dicyclopropylacetic acid (1.12 g, 8.0 mmol) and 5,6-diamino-1-(4-benzyloxycarbonylaminophenethyl)-3-propyluracil (2.93 g, 8.0 mmol) obtained in Reference Examp 1 were used instead of 3-noradamantanecarboxylic acid (2.79 g, 16.8 mmol) and 5,6-diamino-1-(4-benzyloxycarbonylaminophenethyl)-3-propyluracil (6.12 g, 14.0 mmol) obtained in Reference Example 1.

Melting point: 184.7°–184.9° C.
Elementary analysis for C$_{23}$H$_{29}$N$_5$O$_2$,
Calc. (%): C 67.78, H 7.17, N 17.19
Found (%): C 67.95, H 7.37, N 16.97
IR (KBr) ν$_{max}$ (cm$^{-1}$): 1693, 1646, 1552, 1517, 1495
NMR (270 MHz; DMSO-d$_6$) δ(ppm): 13.06 (1H, brs), 6.83 (2H, d, J=S.3 Hz), 6.46 (2H, d, J=8.3 Hz), 4.84 (2H, brs), 4.11 (2H, t, J=7.1 Hz), 3.83 (2H, t, J=6.9 Hz), 2.79 (2H, t, J=7.9 Hz), 1.60–1.45 (3H, m), 1.30–1.15 (2H, m), 0.86 (3H, t, J=7.4 Hz), 0.65–0.50 (2H, m), 0.40–0.25 (4H, m), 0.25–0.10 (2H, m)
MS (m/e): 407 (M+)

EXAMPLE 4

1-(4-Aminophenethyl)-8-dicyclopropylmethyl-3-propylxanthine (compound 4, 0.25 g) was obtained (yield: 20%) according to the same procedure as that described in Example 1, except that dicyclopropylacetic acid (0.73 g, 5.2 mmol) and 5,6-diamino-3-(4-benzyloxycarbonylaminophenethyl)-1-propyluracil (1.71 g, 4.67 mmol) obtained in Reference Example 2 were used instead of 3-noradamantanecarboxylic acid (2.79 g, 16.8 mmol) and 5,6-diamino-1-(4-benzyloxycarbonylaminophenethyl)-3-propyluracil (6.12 g, 14.0 mmol) obtained in Reference Example 1, respectively.

Melting point: 190.7°–193.2° C.
Elementary analysis for C$_{23}$H$_{29}$N$_5$O$_2$,
Calc. (%): C 67.78, H 7.17, N 17.19
Found (%): C 67.67, H 7.35, N 16.93
IR (KBr) ν$_{max}$ (cm$^{-1}$): 1694, 1652, 1532, 1516, 1496
NMR (270 MHz; DMSO-d$_6$) δ(ppm): 13.08 (1H, brs), 6.87 (2H, d, J=8.5 Hz), 6.48 (2H, d, J=8.5 Hz), 4.86 (2H, brs), 4.10–3.90 (4H, m), 2.64 (2H, t, J=7.9 Hz), 1.75–1.50 (3H, m), 1.30–1.15 (2H, m), 0.87 (3H, t, J=7.4 Hz), 0.60–0.50 (2H, m), 0.40–0.25 (4H, m), 0.20–0.10 (2H, m)
MS (m/e): 407 (M+)

EXAMPLE 5

3 (4-Aminophenethyl)-8-[(1R*, 2R*, 5R*)bicyclo[3.3.0]octan-2-yl]-1,3-dipropylxanthine (Compound 5, 1.48 g) was obtained (yield: 25%) according to the same procedure as that described in Example 1, except that bicyclo[3.3.0]octane-2-carboxylic acid (1.70g, 11.0 mmol) and 5,6-diamino-1-(4-benzyloxycarbonylaminophenethyl)-3-propyluracil (4.00 g, 9.14 mmol) obtained in Reference Example 1 were used instead of 3-noradamantanecarboxylic acid (2.79 g, 16.8 mmol) and 5,6-diamino-1-(4-benzyloxycarbonylaminophenethyl)-3-propyluracil (6.12 g, 14.0 mmol) obtained in Reference Example 1.

Melting point: 237.1°–238.1° C.
Elementary analysis for $C_{24}H_{31}N_5O_2$
Calc. (%): C 68.38, H 7.41, N 16.61
Found (%): C 68.09, H 7.67, N 16.58
IR (KBr) $\nu_{max}$ (cm$^{-1}$): 1700, 1641, 1554, 1505
NMR (270 MHz; CDCl$_3$) δ(ppm): 12.27, (1H, brs), 7.08 (2H, d, J=8.4 Hz), 6.61 (2H, d, J=8.4 Hz), 4.31 (2H, t, J=7.9 Hz), 4.01 (2H, t, J=7.8 Hz), 3.57 (2H, brs), 2.97 (2H, t, J=7.9 Hz), 2.90–2.65 (3H, m), 2.20–1.25 (12H, m), 0.97 (3H, t, J=7.3 Hz)
MS (m/e): 421 (M+)

EXAMPLE 6

3-(4-Aminophenethyl)-8-[(1R*, 2S*, 5S*)-bicyclo[2.2.1]heptan-2-yl]-3-propylxanthine and (1R*, 2R*, 5S*)isomer (1:1 mixture) (Compound 6, 1.47 g) was obtained (yield: 40%) according to the same procedure as that described in Example 1, except that bicyclo[2.2.1]heptane-2-carboxylic acid (1.54 g, 11.0 mmol) and 5,6-diamino-1-(4-benzyloxycarbonylaminophenethyl)-3-propyluracil (4.0 g, 9.14 mmol) obtained in Reference Example 1 were used instead of 3-noradamantanecarboxylic acid (2.79 g, 16.8 mmol) and 5,6-diamino-1-(4-benzyloxycarbonylaminophenethyl)-3-propyluracil (6.12 g, 14.0 mmol) obtained in Reference Example 1.

Melting point : 258.3°–260.2° C.
IR (KBr) $\nu_{max}$ (cm$^{-1}$): 1704, 1649, 1520, 1496
NMR (270 MHz; DMSO) δ(ppm): 12.99 (1H, brs), 6.83 (2x½H, d, J=8.4 Hz), 6.82 (2x½H, d, J=8.4 Hz), 6.45 (2H, d, J=8.4 Hz), 4.86 (2H, brs), 4.11 (2x½H, t, J=7.4 Hz), 4.09 (2x½H, t, J=7.4 Hz), 3.81 (2H, t, J=7.0 Hz), 3.25–3.15 (½H, m), 2.80–2.70 (½H+2H, m), 2.60–2.25 (2H, m), 2.10–1.10 (10H, m), 0.85 (3H, t, J=7.4 Hz)
MS (m/e): 407 (M+)

REFERENCE EXAMPLE 1

4-Nitrophenethylamine (127 g, 0.767 mol) [J. Org. Chem., 43, 31(1978)] was dissolved in toluene (2.5 liters), and propyl isocyanate (72 ml, 0.764 mol) was slowly added dropwise to the solution at room temperature. After stirring for 2 hours, the crystals formed were collected and dried under reduced pressure to obtain 1-(4-nitrophenethyl)-3-propylurea [compound (a)] (171.5 g, yield: 89.8%).

IR (KBr) $\nu_{max}$ (cm$^{-1}$): 3322, 2870, 1620, 1578, 1516
NMR (CDCl$_3$, 90 MHz) δ(ppm): 8.10 (2H, d, J=8.8 Hz), 7.35 (2H, d, J=8.8 Hz), 4.95–4.50 (2H, m), 3.70–3.30 (2H, m), 3.25–2.75 (6H, m), 1.70–1.30 (2H, m), 0.90 (3H, t, J=7.0 Hz)

The compound (a) (170 g, 0.677 mol) and cyanoacetic acid (63.3 g, 0.744 mol) were dissolved in acetic anhydride (196 ml) and reacted at 75° C. for 2 hours. The reaction mixture was concentrated under reduced pressure, water (200 ml) was added thereto and the mixture was concentrated again under reduced pressure. The resulting crude crystals were recrystallized twice from ethyl acetate to give 1-cyanoacetyl-3-(4-nitrophenethyl)-1-propylurea [compound (b)] (42.9 g, yield: 19.9%). The filtrate obtained from recrystallization was concentrated under reduced pressure and the residue was purified on silica gel column chromatography (eluent: 2% methanol/98% chlorofom) to give the compound (b) (62.2 g, yield 29%) and 1-cyanoacetyl-1-(4-nitrophenethyl)-3-propylurea [compound (c)] (45.0 g, yield: 21%).

Compound (b):
IR (KBr) $\nu_{max}$ (cm$^{-1}$): 3386, 2876, 2260, 1693, 1678, 1518, 1503
NMR (CDCl$_3$, 90 MHz) δ(ppm): 8.55 (1H, brs), 8.16 (2H, d, J=8.7 Hz), 7.38 (2H, d, J=8.7 Hz), 3.78 (2H, s), 3.80–3.45 (4H, m), 3.01 (2H, t, J=7.0 Hz), 1.80–1.40 (2H, m), 0.99 (3H, t, J=7.0 Hz)
MS (m/e): 318 (M+)

Compound (c):
NMR (90 MHz; CDCl$_3$) δ(ppm): 8.17 (2H, d, J=8.5 Hz), 7.36 (2H, d, J=8.5 Hz), 3.90 (2H, t, J=7.5 Hz), 3.63 (2H, s), 3.40–3.00 (4H, m), 1.61 (2H, s), 1.80–1.40 (2H, m), 0.96 (3H, t, J=7.0 Hz)

2N Aqueous solution (680 ml) of sodium hydroxide was added to the resulting compound (b) (57.5 g, 0.181 mol) and the mixture was stirred at 75° C. for 30 minutes. After cooling, the resulting crystals were collected, washed with water and dried under reduced pressure to obtain 6-amino-1-(4-nitrophenethyl)-3-propyluracil [compound (d)] (51.7 g, yield: 89.7%).

IR (KBr) $\nu_{max}$ (cm$^{-1}$): 1658, 1639, 1611, 1518, 1492
NMR (90 MHz; DMSO-d$_6$) δ(ppm): 8.10 (2H, d, J=8.5 Hz), 7.47 (2H, d, J=8.5 Hz), 6.82 (2H, brs), 4.78 (1H, s), 4.08 (2H, t, J=7.2 Hz), 1.65–1.15 (2H, m), 0.77 (3H, t, J=7 Hz)
MS (m/e): 318 (M+)

The compound (d) (20 g, 62.8 mmol) was dissolved in acetic acid (100 ml) and 10% Pd/C (lg) was added thereto. The mixture was stirred for 8 hours under hydrogen. The reaction mixture was filtered and the filtrate was concentrated under reduced pressure and made alkaline by the addition of 1N aqueous solution of sodium hydroxide. The precipitated crystals were collected by filtration, washed with water and dried under reduced pressure to obtain 6-amino-1-(4-aminophenethyl)-3-propyluracil [compound (e)] (15.6 g, yield: 86.5%).

IR (KBr) $\nu_{max}$ (cm$^{-1}$): 1658, 1613, 1517
NMR (90 MHz; CDCl$_3$) δ(ppm): 7.00 (2H, d, J=8.0 Hz), 6.67 (2H, d, J=8.0 Hz), 4.82 (1H, s), 4.20–3.70 (6H, m), 2.90 (2H, t, J=7.5 Hz), 1.80–1.50 (4H, m), 0.95 (3H, t, J=7.2 Hz)
MS (m/e): 288 (M+)

The compound (e) (7 g, 24.3 mmol) was dissolved in tetrahydrofuran (180 ml) and water (120 ml) and sodium bicarbonate (4.13 g, 49.2 mmol) were added thereto. This solution was cooled to 5° to 10° C., and 30% solution (11.9 g, 20.8 mmol) of carbobenzoxy chloride in toluene was added dropwise thereto while maintaining pH at 8 to 9 with 2N aqueous solution of sodium hydroxide. The mixture was then stirred for 30 minutes and concentrated under reduced pressure. Water was added thereto and the precipitate was collected. The precipitate was dissolved in ethyl acetate (500 ml) by heating and the solution was dried over sodium sulfate and then the solvent was evaporated under reduced pressure to obtain 6-amino-1-(4-benzyloxycarbonylaminophenethyl)-3-propyluracil [compound (f)] (10.0 g, yield: 98.0%).

IR (KBr) $\nu_{max}$ (cm$^{-1}$): 1706, 1660, 1606, 1527, 1511
NMR (90 MHz; DMSO-d$_6$) δ(ppm): 8.63 (1H, brs), 7.65–7.20 (7H, m), 7.11 (2H, d, J=8.5 Hz), 5.15 (2H, s), 4.67 (1H, s), 3.99 (2H, t, J=7.0 Hz), 3.62 (2H, t, J=7.5

Hz), 2.73 (2H, t, J=7.0 Hz), 1.55–1.25 (2H, m), 0.78 (3H, t, J=7.5 Hz)

MS (m/e): 422 (M+)

The compound (f) (6.3 g, 14.0 mmol) was dissolved in a mixture of ethanol (120 ml) and water (40 ml) and conc. hydrochloric acid (2.87 ml) was added thereto at 30° C., followed by sodium nitrite (1.82 g, 26.4 mmol). After stirring for about 30 minutes, the precipitated purplish red crystals were collected, washed with water and dried under reduced pressure to obtain 6-amino-1-(4-benzyloxycarbonylaminophenethyl)-5-nitroso-3-propyluracil [compound (g)] (8.66g, yield: 82.3%).

Melting point: 192.5°–194.5° C.

IR (KBr) $\nu_{max}$ (cm$^{-1}$): 1730, 1670, 1642, 1527, 1515

NMR (90 MHz; DMSO-d$_6$) δ(ppm): 9.62 (1H, brs), 7.45–7.20 (7H, m), 7.08 (2H, d, J=8.8 Hz), 5.12 (2H, s), 4.06 (2H, t, J=7.5 Hz), 3.79 (2H, t, J=7.0 Hz), 2.75 (2H, t, J=7.5 Hz), 1.70–1.25 (2H, m), 0.84 (3H, t, J=7.0 Hz)

MS (m/e): 451 (M+)

The compound (g) (6.3 g, 14.0 mmol) was suspended in 50% aqueous solution (280 ml) of ethanol, and sodium hydrosulfite (9.7 g, 55.7 mmol) was added slowly thereto with stirring over 30 minutes. After insoluble materials were removed by filtration, the filtrate was concentrated under reduced pressure. The resulting crystals were collected, washed with water and dried under reduced pressure to obtain 5,6-diamino-1-(4-benzyloxycarbonyl-aminophenethyl)-3-propyluracil (5.23 g, yield: 85.7%).

MS (m/e): 437 (M+)

REFERENCE EXAMPLE 2

2N Aqueous solution (680 ml) of sodium hydroxide was added to the compound (c) (25.3 g, 79.6 mmol). The mixture was stirred at 75° C. for 30 minutes. The mixture was cooled, the precipitated crystals were filtered off, washed with water and dried under reduced pressure to obtain 6-amino-3-(4-nitrophenethyl)-1-propyluracil [compound (h)] (20.0 g, yield: 70%).

IR (KBr) $\nu_{max}$ (cm$^{-1}$): 1658, 1643, 1608, 1585, 1516, 1344

NMR (90 MHz; DMSO-d$_6$) δ(ppm): 8.50 (2H, d, J=8.5 Hz), 7.48 (2H, d, J=8.5 Hz), 6.81 (2H, brs), 4.67 (1H, s), 4.00 (2H, t, J=7.3 Hz), 3.72 (2H, t, J=7.5 Hz), 2.93 (2H, t, J=7.5 Hz), 1.70–1.20 (2H, m), 0.81 (3H, t, J=7.0 Hz)

MS (m/e): 318 (M+)

6-Amino-3-(4-aminophenethyl)-1-propyluracil [compound (i)] (9.78 g, yield: 100%) was obtained using the compound (h) (10.8 g, 32.9 mmol) according to the same procedure as that described in Reference Example 1 for obtaining the compound (e) from the compound (d).

IR (KBr) $\nu_{max}$ (cm$^{-1}$): 1686, 1608, 1516, 1494

NMR (90 MHz; DMSO-d$_6$) δ(ppm): 6.78 (2H, d, J=8.0 Hz), 6.78 (2H, brs), 6.45 (2H, d, J=8.0 Hz), 4.78 (2H, brs), 3.93–3.50 (4H, m), 2.65–2.40 (2H, m), 1.70–1.20 (2H, m), 0.86 (3H, t, J=7.0 Hz)

MS (m/e): 288 (M+)

6-Amino-3-(4-benzyloxycarbonylaminophenethyl)-1propyluracil [compound (j)] (13.25 g, yield: 95%) was obtained using the compound (i) (9.78 g, 33.9 mmol) according to the same procedure as that described in Reference Example 1 for obtaining the compound (f) from the compound (e).

IR (KBr) $\nu_{max}$ (cm$^{-1}$): 1722, 1689, 1657, 1651, 1614, 1525

NMR (90 MHz; DMSO-d$_6$) δ(ppm): 9.62 (1H, s), 7.50–7.15 (7H, m), 7.00 (2H, d, J=9 Hz), 6.63 (2H, brs), 5.08 (2H, 3.95–3.50 (4H, m), 2.65 (2H, t, J=7.5 Hz), 1.70–1.20 (2H, m), 0.86 (3H, t, J=7.0 Hz)

MS (m/e): 422 (M+)

6-Amino-3-(4-benzyloxycarbonylaminophenethyl)-5-nitroso-1-propyluracil [compound (k)] (12.2 g, yield 87%) was obtained using the compound (j) (13.2 g, 31.1 mmol) according to the same manner as that described in Reference Example 1 for obtaining the compound (g) from the compound (f).

IR (KBr) $\nu_{max}$ (cm$^{-1}$): 1720, 1704, 1650, 1640, 1542, 1527

MS (m/e): 451 (M+)

5,6-Diamino-3-(4-benzyloxycarbonylaminophenethyl)-1-propyluracil (0.8 g, yield 83%) was obtained using the compound (k) (1 g, 2.21 mmol) according to the same manner as that described in Reference Example 1 for obtaining the end compound from the compound (g).

MS (m/e): 437 (M+)

What is claimed is:

1. A xanthine derivative of the formula (I):

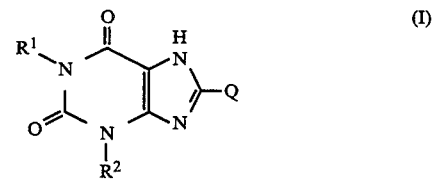

wherein one of R$^1$ and R$^2$ represents lower alkyl which is optionally substituted with alloyclio alkyl having 3 to 8 carbon atoms, lower alkenyl, lower alkynyl, alicyclic alkyl (which is optionally substituted with 1 to 3 substituents independently selected from the group consisting of alkyl having 1 to 6 carbon atoms, hydroxy, alkoxy having 1 to 6 carbon atoms, halogen, nitro and amino), phenyl (which is optionally substituted with 1 to 3 substituents independently selected from the group consisting of alkyl having 1 to 6 carbon atoms, hydroxy, alkoxy having 1 to 6 carbon atoms, halogen, nitro and amino), or benzyl (which is optionally substituted with 1 to 3 substituents independently selected from the group consisting of lower alkyl having 1 to 6 carbon atoms, hydroxy, alkoxy having 1 to 6 carbon atoms, halogen, nitro and amino); and the other represents —(CH$_2$)$_m$—X wherein m is 2 or 3, and X is

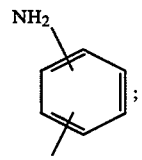

Q represents

(wherein R$^3$ and R$^4$ are independently substituted or unsubstituted alicyclic alkyl),

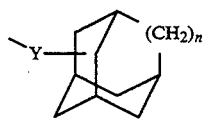

(wherein Y is single bond or alkylene; and n is 0 or 1),

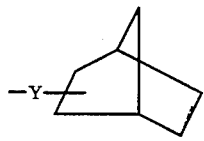

(wherein ═ is single or double bond), or

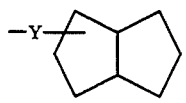

; or a pharmacologically acceptable salt thereof.

2. The xanthine compound according to claim 1, wherein one of $R^1$ and $R^2$ represents unsubstituted lower alkyl; and the other represents

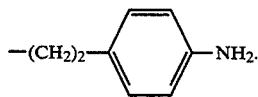

3. The xanthine compound according to claim 2, wherein Q is

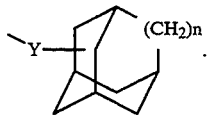

4. The compound according to claim 1, wherein said salt is selected from the group consisting of acid addition salts, metal salts, ammonium salts and organic amine addition salts.

5. A pharmaceutical composition comprising a pharmacologically acceptable carrier and, as an active ingredient, the derivative as defined by claim 1.

* * * * *

UNITED STATES PATENT AND TRADEMARK OFFICE
CERTIFICATE OF CORRECTION

PATENT NO. : 5,447,933

DATED : September 5, 1995

INVENTOR(S) : FUMIO SUZUKI ET AL.     Page 1 of 2

It is certified that error appears in the above-identified patent and that said Letters Patent is hereby corrected as shown below:

Title page, col. 2,

AT [56] REFERENCES CITED

Foreign Patent Documents,
"3173888" should read --3-173888--.
"3173889" should read --3-173889--.

COLUMN 3

Line 12, "and" (second occurrence) should be deleted.

COLUMN 7

Line 7, "N " should read --N --.
         |           |
         $R^5$       $R^6$ Line 34, "tertbutoxycarbo-" should read --tert-butoxycarbo- --.

COLUMN 8

Line 19, "(Process S)," should read --(Process B),--.

COLUMN 11

Line 50, "whister" should read --wistar--.

COLUMN 13

Line 34, "The compound 1," should read --Compounds 1,--.

UNITED STATES PATENT AND TRADEMARK OFFICE
CERTIFICATE OF CORRECTION

PATENT NO. : 5,447,933
DATED : September 5, 1995
INVENTOR(S) : FUMIO SUZUKI ET AL.

It is certified that error appears in the above-identified patent and that said Letters Patent is hereby corrected as shown below:

COLUMN 14

Line 41, "ages" should read --age--.

COLUMN 16

Line 18, "Examp 1" should read --Example 1--.
Line 29, "J=S.3Hz)," should read --J=8.3Hz),--.
Line 62, "3   (4-" should read --3-(4- --.

COLUMN 19

Line 60, "1propyluracil" should read --1-propyluracil--.

COLUMN 20

Line 1, "(2H," should read --(2H, s),--.
Line 33, "$R^{\ell}$" should read --$R^1$--.
Line 34, "alloyclio" should read --alicyclic--.

Signed and Sealed this

Ninth Day of April, 1996

Attest:

BRUCE LEHMAN

Attesting Officer

Commissioner of Patents and Trademarks